US007049130B2

(12) United States Patent
Carroll et al.

(10) Patent No.: US 7,049,130 B2
(45) Date of Patent: *May 23, 2006

(54) DIAGNOSTIC SANITARY TEST STRIP

(75) Inventors: Patrick Carroll, Ft. Lauderdale, FL (US); Jon Schneider, Weston, FL (US); Douglas E. Bell, Coral Springs, FL (US)

(73) Assignee: Home Diagnostics, Inc., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/084,007

(22) Filed: Mar. 21, 2005

(65) Prior Publication Data

US 2005/0164406 A1  Jul. 28, 2005

Related U.S. Application Data

(60) Division of application No. 09/984,948, filed on Oct. 31, 2001, which is a continuation-in-part of application No. 09/939,834, filed on Aug. 28, 2001, now abandoned, which is a continuation of application No. 09/938,598, filed on Aug. 27, 2001, now abandoned, which is a continuation of application No. 09/344,895, filed on Jun. 25, 1999, now Pat. No. 6,284,550, which is a division of application No. 08/872,088, filed on Jun. 10, 1997, now Pat. No. 6,040,195.

(51) Int. Cl.
*C12M 3/00* (2006.01)

(52) U.S. Cl. .............. 435/287.2; 422/55; 422/56; 422/57; 422/58; 422/61; 435/11; 435/14; 435/174; 435/180; 435/287.1; 435/287.7; 435/287.8; 435/287.9; 435/805; 435/810; 435/970; 436/66; 436/71; 436/164; 436/169; 436/170; 436/514; 436/518; 436/531; 436/805; 436/810; 436/815; 436/827

(58) Field of Classification Search ............ 422/55–58, 422/61; 435/11, 14, 174, 180, 287.1, 287.2, 435/287.7, 287.8, 287.9, 805, 810, 970; 436/66, 436/71, 164, 169, 170, 514, 518, 531, 805, 436/810, 815, 827
See application file for complete search history.

(56) References Cited

U.S. PATENT DOCUMENTS

| | | | |
|---|---|---|---|
| 3,298,789 A | 1/1967 | Mast | |
| 3,630,957 A | 12/1971 | Rey et al. | |
| 3,844,717 A | 10/1974 | Sodickson et al. | |
| 3,992,158 A | 11/1976 | Przybylowicz | |
| 4,059,405 A | 11/1977 | Sodickson | |
| 4,199,261 A | 4/1980 | Tidd | |
| 4,627,445 A | 12/1986 | Garcia | |
| 4,637,403 A | 1/1987 | Garcia | |
| 4,668,472 A * | 5/1987 | Sakamoto et al. ............ 422/56 |
| 4,719,085 A * | 1/1988 | Jacobs ......................... 422/56 |
| 4,774,192 A | 9/1988 | Terminiello | |
| 4,787,398 A | 11/1988 | Garcia | |
| 4,790,979 A | 12/1988 | Terminiello | |
| 4,818,677 A * | 4/1989 | Hay-Kaufman et al. ....... 435/4 |
| 4,826,759 A * | 5/1989 | Guire et al. .................. 435/4 |
| 4,877,580 A | 10/1989 | Aronowitz | |
| 4,935,346 A | 6/1990 | Phillips et al. | |
| 4,987,085 A | 1/1991 | Allen et al. | |
| 4,994,238 A | 2/1991 | Daffern et al. | |
| 5,049,487 A | 9/1991 | Phillips et al. | |
| 5,059,394 A | 10/1991 | Phillips et al. | |
| 5,179,005 A | 1/1993 | Phillips et al. | |
| 5,284,622 A | 2/1994 | Krause et al. | |
| 5,296,192 A | 3/1994 | Carroll et al. | |
| 5,304,468 A | 4/1994 | Phillips et al. | |
| 5,426,032 A | 6/1995 | Phillips et al. | |
| 5,563,042 A | 10/1996 | Phillips et al. | |
| 5,738,828 A | 4/1998 | Stoughton | |
| 5,780,304 A | 7/1998 | Matzinger et al. | |
| 5,843,692 A | 12/1998 | Phillips et al. | |
| 6,040,195 A | 3/2000 | Carroll et al. | |
| 6,268,162 B1 | 7/2001 | Phillips et al. | |
| 6,284,550 B1 | 9/2001 | Carroll et al. | |

FOREIGN PATENT DOCUMENTS

EP  0169055  1/1986

* cited by examiner

Primary Examiner—Christopher L. Chin
(74) Attorney, Agent, or Firm—Finnegan, Henderson, Farabow, Garrett & Dunner, L.L.P.

(57) ABSTRACT

An improved multi-layered diagnostic sanitary test strip for receiving a heterogenous fluid, such as whole blood, to test for presence and/or amount of a suspected analyte in the fluid by facilitating a color change in the strip corresponding to the amount of the analyte in the fluid, wherein the test strip includes fluid volume control dams to prevent spillage of the fluid from the strip and a chemical reagent solution that facilitates end-point testing. The improved test strip comprises no more than two operative layers and: (a) a reaction membrane containing a reagent capable of reacting with the analyte of interest to produce a measurable change in said membrane; (b) an upper support layer defining a sample receiving port for receiving the fluid sample thereat; (c) one or more structures for directing the sample containing the analyte of interest through at least a portion of said reaction membrane; and (d) a lower support layer having a reaction viewing port in vertical alignment with said membrane for displaying said measurable change, said lower support being associated with said upper support to secure said reaction membrane in said test strip.

34 Claims, 6 Drawing Sheets

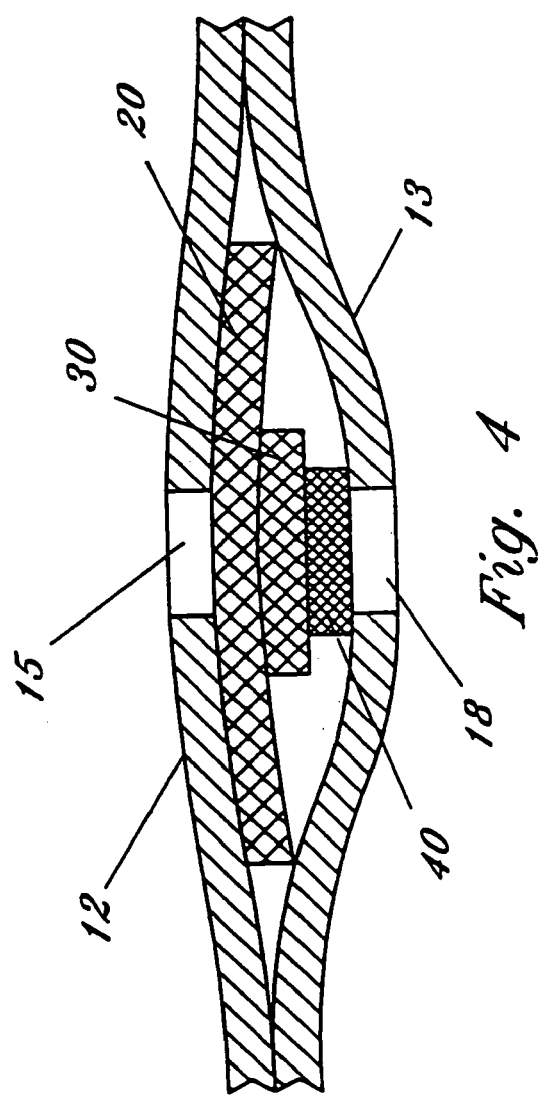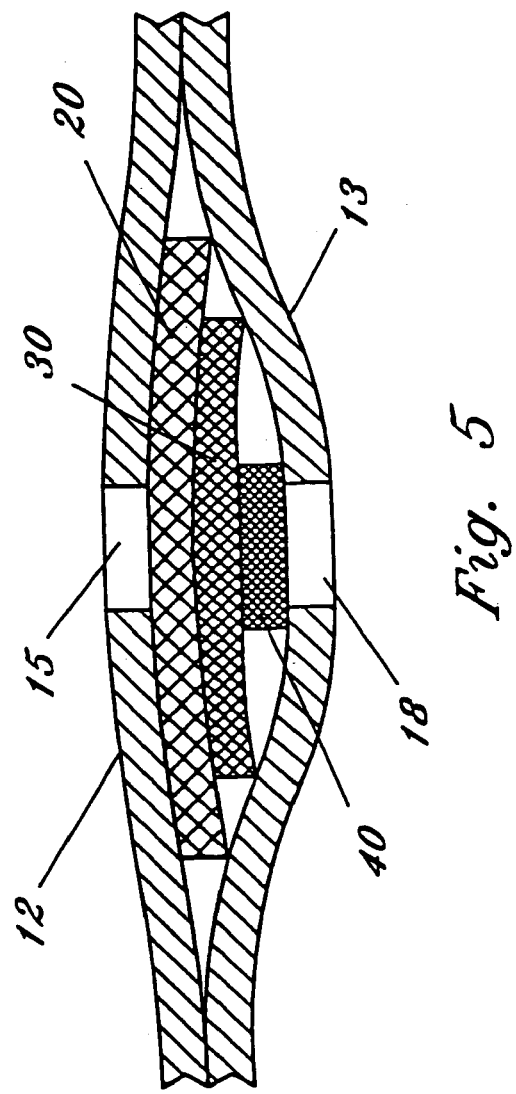

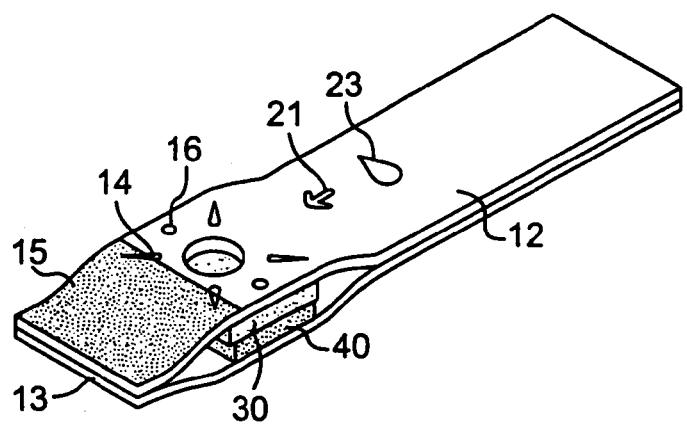
FIG. 6
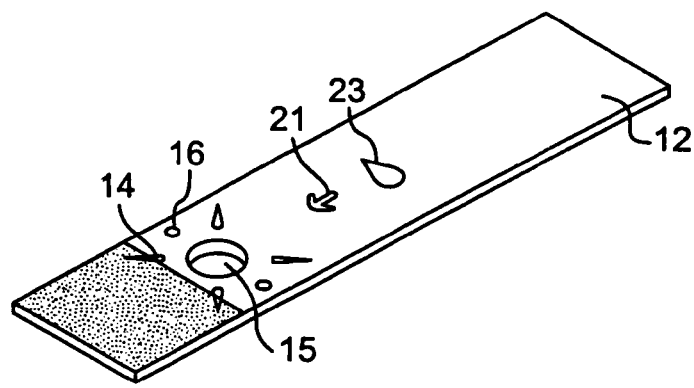
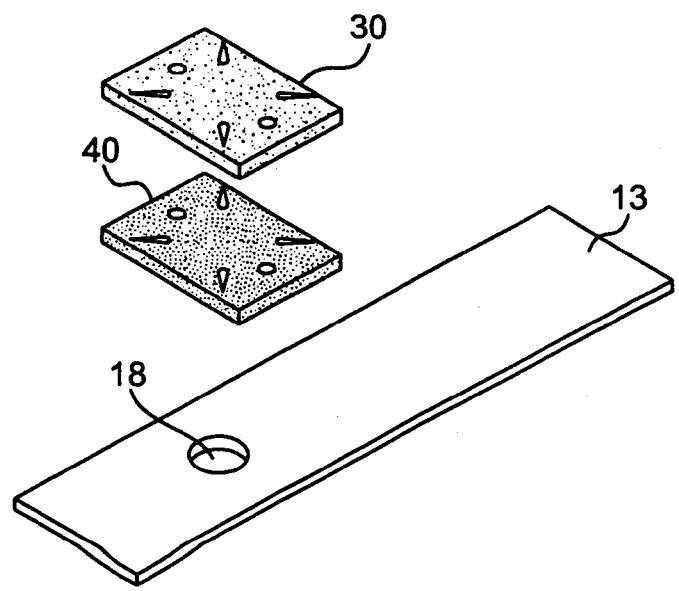
FIG. 7

DIAGNOSTIC SANITARY TEST STRIP

CROSS-REFERENCE TO RELATED APPLICATIONS

This is a Divisional of application Ser. No. 09/984,948, filed Oct. 31, 2001, which is a Continuation-In-Part of application Ser. No. 09/939,834, filed Aug. 28, 2001 now abandoned, which is a Continuation of application Ser. No. 09/938,598, filed Aug. 27, 2001, now abandoned, which is a Continuation of application Ser. No. 09/344,895, filed Jun. 25, 1999, now U.S. Pat. No. 6,284,550, issued Sep. 4, 2001, which is a Divisional of application Ser. No. 08/872,088, filed Jun. 10, 1997, now U.S. Pat. No. 6,040,195, issued Mar. 21, 2000, all of which disclosures are incorporated herein by reference.

FIELD OF THE INVENTION

This invention relates generally to analytical test strip devices, and more particularly to an improved diagnostic sanitary test strip device for determining the presence, absence, and/or amount of a predetermined analyte, and having a fluid sample volume control, structure to facilitate proper orientation of the strip in a corresponding meter, and an improved agent treatment solution for facilitating end-point testing.

DESCRIPTION OF THE BACKGROUND ART

Analytical test strips for testing analytes in heterogeneous fluid samples are well known in the art and comprise various structures and materials. These test strips typically include single or multi-layered fibrous membrane devices which receive a heterogeneous fluid, such as whole blood, and undergo a color change in response to interaction with agents/reactants imbibed into the membrane. Prior to reaching the reactants, the fluid sample is filtered to facilitate accurate testing of the analyte. For instance, a blood sample being treated for glucose levels requires the removal of red blood cells before testing the plasma. Some test strips include additional layers that provide the requisite filtering. Other test strips attempt to filter and test a sample for a suspected analyte in a single membrane. Terminiello et al., U.S. Pat. No. 4,774,192, teaches such a dry chemistry reagent system which comprises a porous anisotropic (asymmetrical) membrane having a porosity gradient from one planar surface to the other for filtering a fluid sample and includes an indicator, flow control agent, and reagent cocktail imbibed therein for initiating the chemical reaction with the fluid sample. Anisotropic membranes, however, provide inadequate filtering and can have a tendency to produce unreliable results.

Test strip devices operate by allowing the applied heterogeneous sample to migrate to a reaction site in the membrane, where the analyte of interest in the sample reacts with the imbibed agents. The results of the reaction are usually visible through a color change in the membrane. The color change may be viewed with the naked eye and measured by a visual comparison with a color chart or reading it with a reflectance meter.

Certain problems have been noted in existing analytical test strips. Some of these problems include spillage of the sample over the edges of the strip, excessive absorption, and incomplete filtering, all of which can adversely affect test integrity. Other strips, such as those disclosed in U.S. Pat. No. 3,298,789 issued to Mast and U.S. Pat. No. 3,630,957 issued to Rey et al., require the sample to remain in contact with the reagent pad for specified time and that the blood sample be either washed or wiped off the pad. In addition, conventional strips have been known to be difficult to use in terms of the proper amount of heterogeneous fluid to place on the strip. It is also difficult to properly place and/or orient strips in a corresponding meter.

U.S. Pat. No. 5,296,192 (the "'192 patent"), issued to the inventors herein, addresses some of these shortcomings noted in the background art. The '192 patent teaches a multi-layered diagnostic test strip for receiving whole blood on which a test for a suspected analyte is performed. The multi-layered test strip device comprises two outside supports, sandwiching therebetween a spreading screen, a separating layer, and a membrane. The top support has a port for receiving the sample. The spreading screen evenly distributes the sample so that it uniformly passes into the separating layer. The separating layer removes a majority of the red blood cells from the blood sample, and the membrane removes the remaining cells. The membrane is also pretreated with reagents and conditioning agents needed for the reaction and insuring a readable, reliable color generation. The '192 patent provides a strip that may be visually read with a color comparator or a reflectance meter. The instant invention provides an improved diagnostic test strip which is built in part on some of the teachings of the '192 patent, and which has additional features for further enhancing the use and reliability of diagnostic testing. These improvements are submitted as solving the above-noted problems.

SUMMARY OF THE INVENTION

The present invention is directed to an improved, multi-layered sanitary test strip for receiving a heterogenous fluid that is tested for a suspected analyte. In the preferred embodiment, the heterogeneous fluid comprises a whole blood which is analyzed to determine the presence of analytes, such as glucose or cholesterol, to determine the presence, absence, and/or level of the analyte in the fluid. Accordingly, discussion herein is tailored to the receipt and testing of glucose analytes in a whole blood sample. As such, the suggested chemical reagents herein are specific to testing glucose in blood. It is important to note, however, that the instant invention may be used to determine the presence, absence, and/or amount of a substance in other heterogeneous fluids by modifying the chemical reagent solutions and/or concentrations employed. The diagnostic sanitary test strip may be used for other enzymes and immunoassays, such as cholesterol (HDL or LDL), ketones, theophylline, osteoporosis, H1AC, fructosamine and others. The present invention confirms the presence, absence, and/or amount of these analytes.

The multi-layered diagnostic sanitary test strip generally comprises two outside layers, between which are operative layers. Said operative layers comprise, in descending order, an optional spreading layer, a separating layer, a membrane layer. The membrane layer (or reaction membrane, or membrane) may optionally be pretreated with a reagent solution imbibed into the membrane. The multi-layered test strip taught herein improves on the test strip disclosed in U.S. Pat. No. 5,296,192, the disclosure of which is incorporated herein by reference. The instant invention is an improvement in that it provides a chemistry reagent solution and concentration that facilitates end-point testing, volume control dams to prevent spills or overflow and reduce the amount of sample needed to perform a test, and a light absorption medium which visually and functionally prevents the test strip from being tested upside down. The improved, diagnostic test strip also allows for the application of a heterogeneous fluid sample, e.g., blood, to the strip, both inside and outside the meter.

It is an object of the present invention to provide an improved multi-layered diagnostic sanitary test strip.

It is another object of the present invention to provide an improved multi-layered diagnostic sanitary test strip that prevents a heterogenous fluid sample from overflowing from the strip.

It is an additional object of the present invention to provide an improved multi-layered diagnostic sanitary test strip that is easier to use, requires a smaller amount of the heterogenous fluid sample and facilitates application of the sample on the strip when the strip is either outside or inserted in a meter.

It is a further object of the present invention to provide an improved multi-layered diagnostic sanitary test strip that facilitates proper placement and orientation of the strip in a corresponding meter.

It is yet another object of the present invention to provide an improved multi-layered diagnostic sanitary test strip that may be used in a meter that performs end-point testing.

It is yet an additional object of the present invention to provide an improved multi-layered diagnostic sanitary test strip that may be imbibed with a dry chemistry reagent solution that facilitates end-point testing.

In accordance with these and other objects which will become apparent hereinafter, the instant invention will now be described with particular reference to the accompanying drawings.

BRIEF DESCRIPTION OF THE DRAWINGS

FIG. 4 is a cross sectional elevation view of the layers of the test strip as it appears after construction.

FIG. 5 is a cross sectional elevation view of another embodiment of the invention as it appears after construction.

FIGS. 6–10 depict the views of FIGS. 1–5, respectively, wherein the test strip is manufactured without a spreading layer.

DESCRIPTION OF THE PREFERRED EMBODIMENTS

With reference to the drawings, FIGS. 1–10 depict preferred embodiments of the improved, multi-layered diagnostic sanitary test strip 10 of the instant invention. The test strip 10 represents an improvement over prior test strips. It embodies novel features that make the strip more sanitary, spill resistant, easier to use, accommodating of lower sample volumes, and more efficient. In a preferred use, a whole blood sample from a finger stick, or otherwise, is applied to the strip 10 to test for the presence, absence, and/or amount of a suspected analyte, e.g., glucose. It is important to note that whole blood may be tested for other analytes and that other heterogeneous fluid samples may be tested for glucose and other analytes, such as LDH/HDL cholesterol, H1AC, osteoporosis, fructosamine, etc.

The test strip 10 generally comprises an optional spreading layer (e.g., spreading screen) 20, a separating layer 30 for filtering, and a preconditioned membrane 40. The membrane 40, and optionally also the separating layer 30, can be pre treated with reagents and/or conditioning solutions, as discussed more fully herein. During use, the reagents and conditioning system filters the sample so that the analytes of interest can be more easily detected and measured without interference. For example, where blood is used, the novel system according to the invention removes red blood cells from the plasma of the sample so that red blood cells do not interfere with optical measurement.

Figures 1, 2:
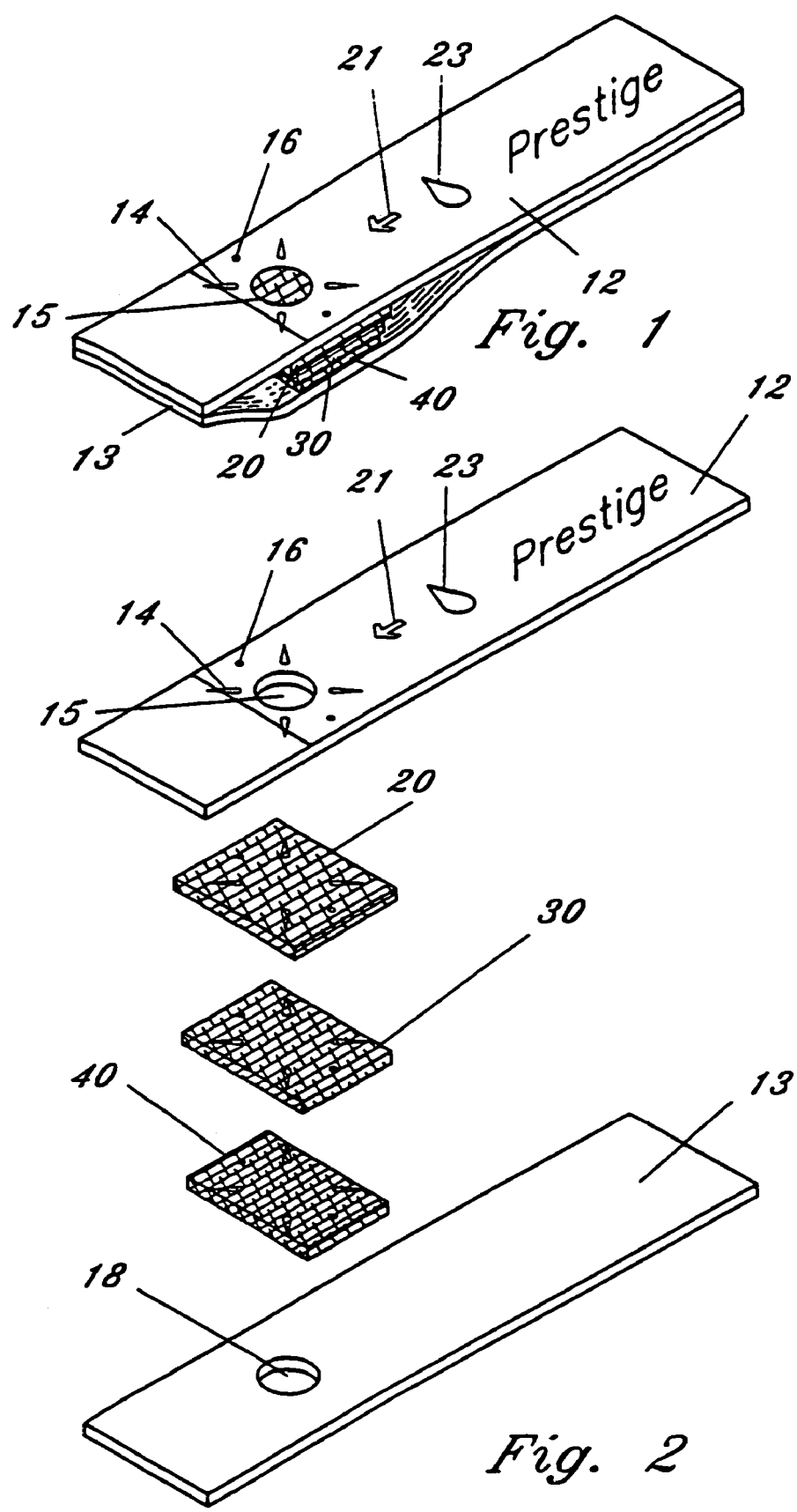
FIG. 1 is a perspective view of the preferred embodiment of the multi-layered diagnostic sanitary test strip of the instant invention.
FIG. 2 is a perspective view of the multi-layered diagnostic sanitary test strip prior to ultrasonically sealing the strip.
Figure 3A:
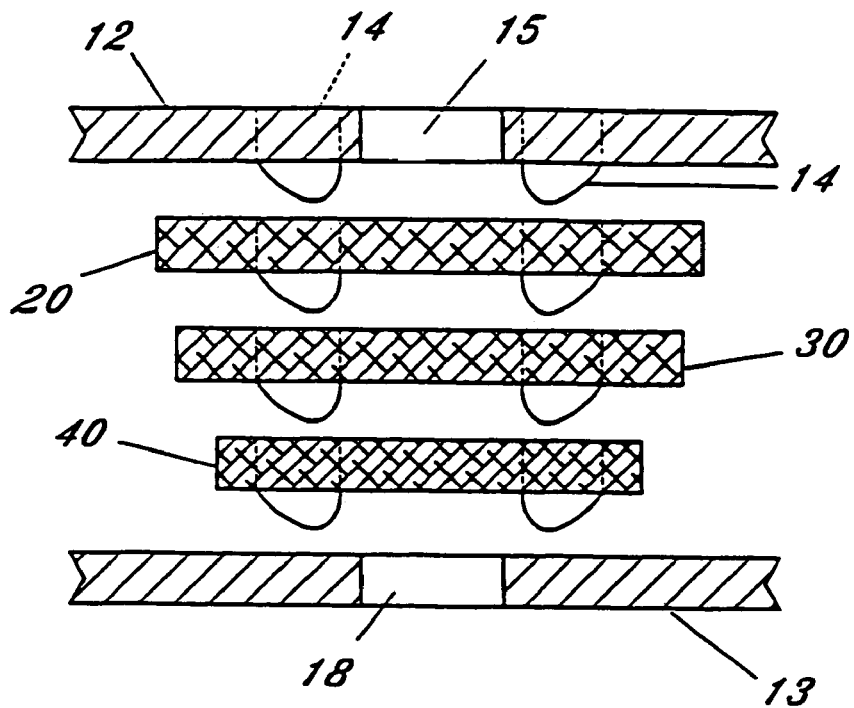
FIG. 3a is an exploded, cross sectional view of the instant invention, taken along lines A—A of FIG. 2.
Figure 3B:
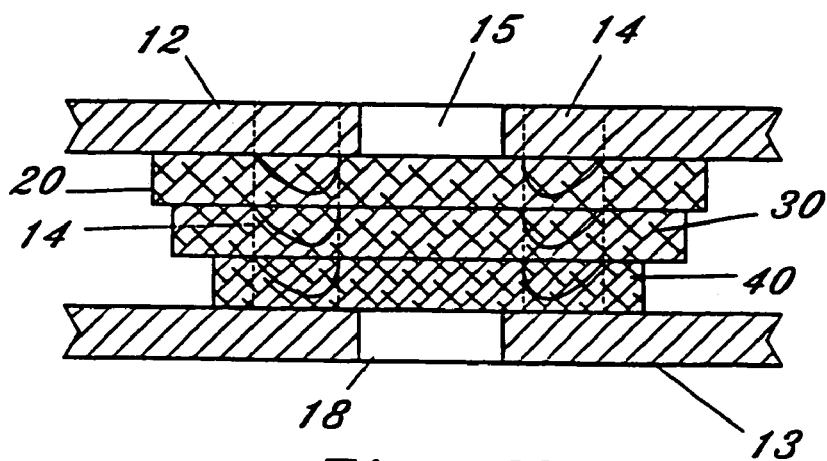
FIG. 3b is a cross sectional view of the instant invention, taken along lines A—A of FIG. 2.
Figure 8A:
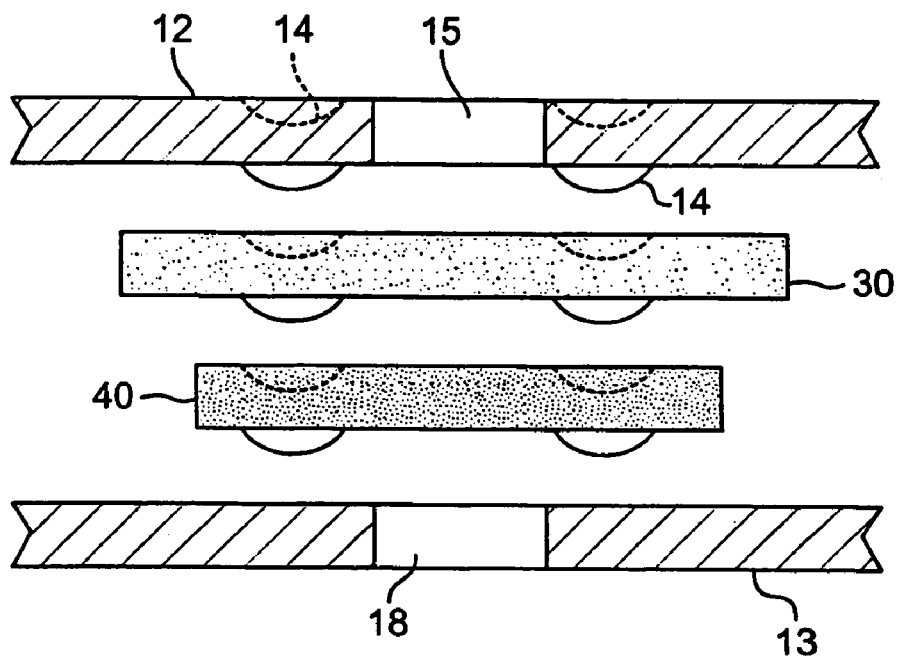
Figure 8B:
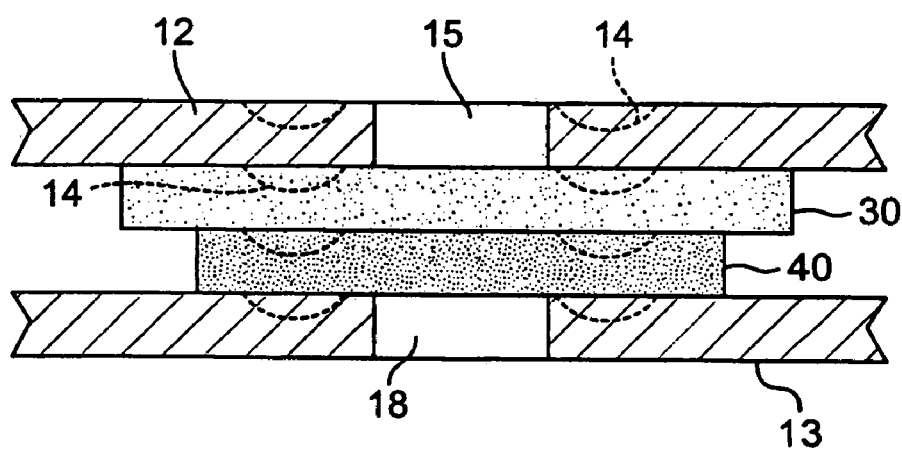

As shown in FIG. 1, the test strip 10 generally comprises an upper support layer 12 and a lower support layer 13 and an optional spreading layer (e.g., a spreading screen) 20, a separating layer 30, and a semi-porous membrane reagent layer 40 sandwiched between in descending order. FIGS. 6–10 depict the views of FIGS. 1–5, respectively, of a test strip constructed without a spreading layer. At least one of layers 20 (when present), 30, and 40 is pretreated with a dry chemistry reagent and conditioning solution. Preferably, the membrane 40 and separating layer 30 are pretreated with the reagent/conditioning solution. The spreading screen 20, if present, may also pretreated. Each layer 20, 30, and 40 is positioned in tight, continuous contact with its adjacent layer as shown in FIGS. 4 and 5 (FIGS. 9 and 10 in a corresponding test strip constructed without a separating layer). The support layers 12, 13, screen 20, separator 30, and membrane 40 are aligned as shown in FIGS. 2, 3a, and 3b (FIGS. 7, 8a, and 8b without the spreading layer 20) and glued and ultrasonically bonded together to provide a sealed composite structure. The support strips 12, 13 may contain a layer of adhesive on their interior surfaces to physically attach the supporting layers 12, 13 in a way that tightly compresses the other layers 20 (when present), 30, and 40 therebetween. The support layers 12, 13 and operative layers 20 (when present), 30, and 40 are further secured by ultrasonic welding. Other welding techniques may be employed, such as heat-stamping.

The support strips 12, 13 are preferably constructed from mylar. The top and bottom support strips 12, 13 each define an aperture or opening therethrough. These apertures or openings are oriented in vertical alignment when constructing the strip. The opening in the upper support strip 12 defines a sample receiving port 15 and the opening in the lower support strip 13 defines a reaction viewing port 18. The spreading screen 20, when present, abuts the interior glue surface 12a of the upper support 12. The separating layer 30 abuts the lower surface of spreading screen 20 and the upper surface of membrane 40. When the spreading screen 20 is absent, the separating layer 30 abuts the lower surface of the upper support layer 12 and the upper surface of membrane 40. The upper surface of membrane 40 abuts the lower surface of separating screen 30 and the membrane lower surface abuts the interior glue surface of the lower support strip 13. The interior layers are oriented in vertical alignment with the sample receiving port 15 and the reaction viewing port 18. This allows the sample received by the strip 10 to pass directly from the receiving port 15 to the viewing port 18. This movement, however, is facilitated and assisted by the operative layers 20 (when present), 30, and 40 of the strip and volume control structure 14 built therein. By the time the sample reaches the viewing port 18 it has undergone a color change indicative of the analyte of interest and is viewable from the viewing port 18.

Volume control dam partitions 14 are formed in the upper support strip 12 around the sample receiving port 15 and depend downward into the strip to control the flow of the sample volume therein. The dam partitions 14 help direct the fluid sample downward toward the viewing port 18. In addition, the dam partitions 14 resist overflow by retaining the sample and guiding the sample to provide a more sanitary diagnostic test strip 12 and decreasing the amount of sample needed to conduct a test. The strip 10 is shown with four dam partitions 14 positioned approximately 90° apart around a substantially circular sample receiving port 15. This orientation enhances volume flow control. It should be noted, however, that the number and configuration of dam partitions 14 may vary without departing from the scope and spirit of the invention so long as fluid sample is properly retained and vertically directed. The dam partitions 14 are formed by either die-stamping or embossing the upper strip 12 when the strip layers 12, 13, 20, 30, and 40 (or 12, 13, 30, and 40) are bound together through ultrasonic welding or stamping. The volume control dam partitions 14 provide a unique feature of the instant invention which makes the strip easier and more comfortable to use. Moreover, the likelihood of sample overflow or spilling is greatly reduced by the novel structure of the instant invention.

In reference to FIGS. 1, 4, and 5, two Branson detents 16 are provided for strengthening the strip and accommodating Branson securing post which may he found on a corresponding meter. The Branson post and detents 16 are designed to interlock when a strip 10 is inserted into a corresponding meter. The dam partitions 14 also serve to enhance the bond between the support strips 12, 13 and operative layers 20, 30, and 40. The bonds formed by the dam partitions 14 and Branson detent 16 result from the application of energy, preferably ultrasonic energy, applied to the upper surface of support strip 12 during assembly. The penetration of the dams 14 and detents 16 are shown by perforated lines and generally comprise deep indentations in the assembled strip 10. The location of the Branson detents 16 correspond to location of the Branson post found in the corresponding meter. The dam partitions 14 are positioned to retain and direct fluid sample in a manner that prevents overflow and facilitates efficient sample flow through the strip 10. The preferred orientation of the dams 14 are shown in FIG. 1.

Figure 9:
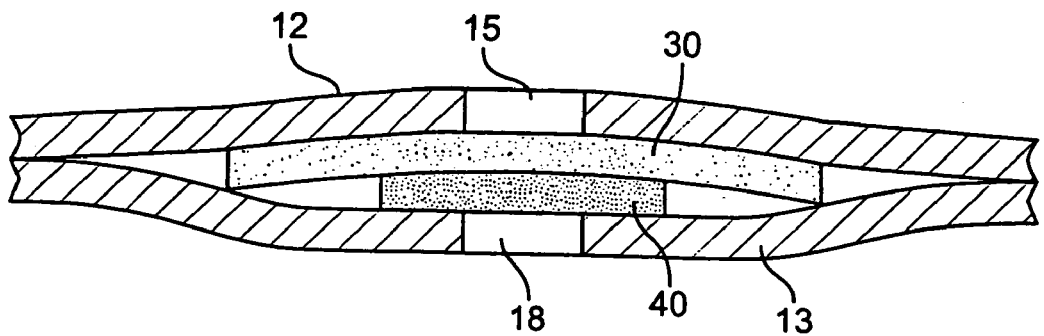
Figure 10:
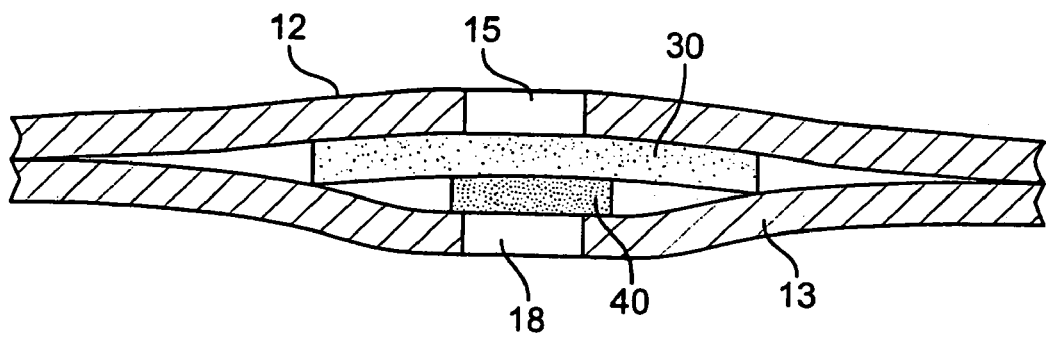

The above noted operative layers 20, 30 and 40 are preferably assembled as shown in FIGS. 1 and 4 using accepted techniques in the art and mylar strips 12, 13 as the support medium for the interior three layers 20, 30 and 40. Operative layers 30 and 40 are preferably assembled as shown in FIGS. 6 and 9 when separating layer 20 is omitted. The inside surfaces of the mylar strips have been previously treated with glue to hold the screen and the reaction membrane in place. In some applications it is desirable to select a separating layer 30 which is slightly larger in width than the reaction membrane 40 so that the edges of the separating layer 30 may overlap the reaction membrane 40 and meet the lower mylar strip 13 at the glued surface to aid further in securing the separating layer 30 to the rest of the device. Referring to FIGS. 2–5, it can be seen that the spreading screen 20 extends beyond the side edges of the separating layer 30 and that the separating layer 30 extends beyond the side edges of the membrane 40. The spreading layer 20 adheres to the upper support strip 12 and the membrane 40 adheres to the lower support strip 13. The support strips 12, 13 are adhered and/or welded together. The spreading screen 20 overextends beyond the separating layer 30 to allow the screen 20 to adhere to the glued surfaces of the support strips 12, 13 and insures a tight, secure connection between layers 20, 30, and 40. When the spreading screen is omitted, the separating layer 30 may optionally overextend beyond the membrane 40 to allow the separating layer to adhere to the glued surface of support strips 12, 13 and insure a tight, secure connection between layers 30 and 40. Once these layers have been assembled, the test strip is inserted into an ultrasonic point welding device and strip welded at the points shown at 14 and 16 in FIG. 1. This results in the volume control dams 14 and Branson holes 16. A suitable strip is two (2) inches long by 0.5 inches wide by 0.035 inches thick with a sample receiving port 15 and reaction viewing port 18 of about 0.2 inches in diameter, preferably sized to snugly fit in the shroud of a corresponding commercially available reflective type meter. When the spreading screen is omitted, these dimensions may be reduced to accommodate smaller volumes of analyte. For instance, a suitable reduced analyte volume test strip can be configured to perform an accurate test with about 3 μl, compared to the prevalent 10 μl for optical test strips. When placed in a meter the Branson holes 16 are intended to align and mate with corresponding posts in the meter. The strip may also be read by comparing the color change in the viewing port 18 to a color chart depicting the amount of analyte found, e.g., glucose.

Proper orientation of the strip 10 in a meter is not always easily ascertainable. To insure that the strip 10 of the instant invention is oriented with the proper surface facing up, the upper surface of the upper support strip 12 includes a light absorption region 19 at one selected end. The light absorption region 19 also serves to indicate the leading end of the strip 10 to be placed in the meter first. Additional indicia in the form of an arrow 21 and blood fluid/fluid drop 23 may also be provided to indicate the direction of insertion and the top surface, respectively. The light absorption region 19 comprises an optically dark, such as black, region adjacent the test area, preferably proximal to the end of the strip. Once inserted, the meter performs a test, such as a light reflection test, to determine whether the strip is properly oriented.

In addition to the foregoing, the strip 10 of the instant invention is designed to allow a blood/heterogeneous fluid sample to be applied to the strip 10 regardless of whether the strip is inserted in or is outside a meter. This is possible because of the volume control provided by the dam partitions 14 and because of the location of the Branson post 16 as shown in FIG. 1.

A spreading screen 20 having a plurality of mesh openings is in contiguous contact with the sample receiving port 15 for receiving and uniformly distributing, or spreading, the heterogeneous fluid over the screen 20. When blood is being analyzed, the sample is typically applied from a finger stick and comprises approximately 15–50 microliters. However, less sample is now required because of the dam partitions 14 provide volume control to limit overflow and direct sample into the strip. This has the added benefit of improved sanitation. The screen 20 is defined by mesh openings that momentarily hold the sample, via surface tension, as the sample uniformly spreads out over the screen 20 to fill the receiving port. Eventually, the sample passes through the screen mesh 20 to the separating layers 30 to deposit an even distribution of the sample onto the separating layer 30. A uniform distribution is required to produce uniform color development. This is important because an uneven distribution of the blood, or other heterogeneous fluid, will cause an uneven distribution to the membrane, which will affect the color change therein and produce an unreliable reading. A preferred screen 20 which may be used with the instant invention is a polyester medical screen, designated PeCap/-7-16/8, provided by Tetko, Inc., Elmsford, N.Y., and having a mesh opening of about 16 microns, a thickness of about 75 microns, and an open area of voids of 8% is. The screen is preferably dipped into a 10% solution of sodium chloride and allowed to dry.

As indicated above, the test strips of the present invention may also be manufactured without a separate spreading screen. The spreading screen 20 may be omitted when, for instance, the separating layer 30 comprises material having sufficient spreading properties. Suitable results have been achieved with separating layers comprising cloth material. Any known or after-discovered material possessing suitable spreading properties with respect to the fluid sample of interest may serve as the separating layer, however. The resulting test strip will thus comprise fewer layers and possess all the advantages inherent therein. Such advantages include, but are not limited to, economies of manufacture and accommodation of smaller analyte sample volumes. The dimensions of the remaining layers and diameters of the sample receiving and viewing ports may also be reduced to accommodate smaller analyte sample volumes, such as 3 µl or less.

Separating layer 30 comprises a pretreated fabric porous screen material placed in contiguous contact with the lower surface of the spreading screen 20. For test strips manufactured without a spreading screen 20, te separating layer 30 may be placed in contiguous contact between the lower surface of the upper support layer 12 and the upper surface of the membrane 40. The treated separating layer 30 removes approximately 80% of the red blood cells from the blood sample. The remaining blood cells are then removed by the membrane 40. A preferred separating layer 30 includes a woven fabric of 50% polyester/50% cotton having mesh openings of about 25 microns, open voids area of 16–20%, and a thickness of about 0.010 inches. The separating layer 30 is treated before assembly with one or more agents that bond or adhere to the red blood cells without lysing them so as to avoid releasing red colorization to the reaction membrane. These bonding agents capture the red blood cells and hold them on the separating layer.

The separating layer 30 should comprise a material that minimizes the absorption of plasma to maximize the plasma which reaches the membrane 40. This is desirable as it results in requiring less blood from the user. If present, the spreading screen 20 is less dense than the separating layer 30. Thus, mesh size openings found in the separating layer 30 are smaller than that for the spreading screen 20, preferably from 20 to 200 microns. The amount of fabric occupied by voids is preferably 15 to 60%. A preferred fabric for the separating layer is polyester, cotton, or a 50/50 polyester-cotton blend.

The separating layer 30 is preferably pretreated with a blood cell separating agent prior to assembly to enhance filtration. The blood cell separating agents imbibed in the separating layer 30 may be any agent known by a practiced artisan to bind to red blood cells without lysing them. These agents include lectins, antibodies to red blood cells, water soluble salts with potassium citrate, ammonium sulfate, zinc sulfate, and the like Lectins are preferred and include proteins or glycoproteins that recognize specific sequences of polysaccharide residues. The lectin or other binding agent is applied by dipping the separating layer fabric into a solution of the lectin or other agent and allowing the wetted fabric to air dry. The solution can be prepared in concentrations that are easily handled in standard test strip manufacturing equipment. Typically, 2–7% solutions are acceptable. The separating layer 30 is preferably dipped into a 2% solution of a lectin derived from kidney beans and allowed to air dry.

Numerous other lectins are commercially available. Some commercially available lectins and the specific sugar residues they recognize are Concanavalin A (Alpha-glucose and alpha-D-mannose), soybean lectin (D-galactose and N-acetyl-D-galactosamine), wheat germ lectin (N-acetyl glucosamine), lotus seed lectin (fucose), potato lectin (N-acetyl glucosamine), dilichos biflorus agglutinin (N-acetyl galactose-aminyl), and legume derived lectins such as lentil lectin (Alpha-D-mannose and alpha-D-glucose).

The membrane 40 is preferably isotropic (symmetrical), that is, uniformly porous. The membrane 40 should be optically white. The membrane 40 provides a medium for holding a reagent and conditioning solution which together produces a color change in the membrane 40 in response to the analyte of interest. In addition, the treated membrane 40 filters the blood sample to remove any remaining red blood cells from the whole blood sample. For other samples, the treated membrane 40 provides necessary filtration as well. A preferred membrane for the detection of glucose analytes comprises a hydrophilic polysulfone membrane having a pore size of 0.2 to 3.0 microns. Such a membrane is manufactured by Gelman Sciences of Ann Arbor, Mich., and has been referred to as Thermopor®. The Supor® 450 membrane is another acceptable membrane which has a pore size of approximately 0.45 microns. Although these membrane are preferred, other isotropic membranes may be used. In fact, membranes produced by other manufacturers may be required for testing analytes other than glucose. Some of these membranes include nylon membranes made by Pall and supported polysulfone membranes made by MSI.

Prior to assembly of the strip 10, the membrane 40 is treated with reagents and conditioning agents in a single dip process. Thereafter, the membrane is allowed to dry. It should be noted that the conditioning process may be other than single dip. Preferably, a six-inch wide membrane of Thermopor®, having a pore size between 0.2 and 3.0 microns is dipped into a solution at seven (7) milliliters of solution per linear foot of membrane. A Supor® 450 membrane having a pore size of approximately 0.45 microns may also be used in place of the Thermopor® and dipped in the same solution at the same rate.

The instant invention comprises a reagent solution that facilitates end-point testing in a corresponding meter. This solution preferably comprises deionized water (700 mL/L), citric acid (tri-sodium salt dihydrate, 52.9 g/L), citric acid (FAM, 4.2 g/L), MAOS (6.6 g/L), 4-Aminoantipyrine (6.1 g/L), 10% Gantrez AN-139 (50 mL/L), polyvinylpyrrolidone and an enzyme solution (100 mL/L). The enzyme solution may include glucose oxidase, peroxidase, 5-dimethoxyaniline, buffers and stabilizers. The prior solution of 4 gms citric acid (free acid monohydrate), 54 g of citric acid (otrisodium salt dihydrate), 60 g polyvinylpyrrolidone, 50 IU/L catalase, 4 g bovin serum albumin (BSA), 0.0055 gm O-Tolidine-Hydrochloride, 0.067 ml. deionized water, 0.0075 gm BSA, 0.0003 gm. glycerol, 11.0 IU peroxidase, 9.5 IV glucose oxidase, 0.002 ml DOSS and 0.003 ml of Gantrez AN-139 may also be used if end-point testing is not conducted.

Best results are obtained from the reaction membrane when it contains, in addition to the specific reagent solution noted above, certain conditioning agents which improve the performance of the reaction membrane. The conditioning agents are generally incorporated into a blend of the reactants in the solution before the latter are incorporated into the reaction membrane. For example, when preparing a reaction layer for a glucose test strip, a base solution is prepared with citric acid, PVP and BSA. This serves as the base to which the chromogen indicator system and other reactants, e.g. peroxidase and glucose oxidase, are added. It has also been found that the color generation by the reaction is stabilized and its readability enhanced by adding a small amount (0.0005–0.009 ml/L of solution) of DOSS (dioctyl sulfosuccinate sodium) available from Sigma Chemical Company. Gantrez AN 139 (a 2.5 furandione polymer with methoxyethene otherwise known as a methyl vinyl ether copolymer with maleic anhydride) at a level of about 0.0005–0.009 ml/L of solution may also be added to aid in conditioning the membrane.

In use, one places a drop of blood of about 25 microliters, from a finger stick for example, into the sample receiving port 15 onto the screen surface. The invention can work well with a sample volume from 10 to 50 microliters of sample.

Prior to the end-point test, a rate test was conducted whereby reflectance was measured by the meter at time equal to forty-five (45) seconds. The rate test; however, does not provide predictable reliability. The end-point test takes reflectance readings at five (5) second increments until successive readings differ by less than five percent (5%). This ensures that the measurement is taken after the reaction has substantially stopped. Since successive measurements are taken until the "end-point" of the reaction, the blood sample may be applied to the strip outside the meter.

The color obtained at the reaction viewing port 18 of the reaction membrane correlates to the amount of glucose in the original sample. The reading can be done by a visual comparison to a color chart of varied and defined color intensities at various concentrations of glucose. It is preferred that a reflectance meter be used to make a reflectance reading of the reacted color. The meter performs a computer analysis by comparing the reflectance reading to standard reflectances obtained on known concentrations of glucose in reaction with the membrane reactants.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A diagnostic test strip for providing an indication of at least one of the presence, the absence or the amount of an analyte of interest in a heterogeneous fluid sample, the test strip comprising:
    a first support layer comprising a sample receiving port for receiving the fluid sample;
    a second support layer comprising a reaction viewing port for displaying the indication;
    a plurality of operative layers between the first and second support layers, the first and second support layers securing the plurality of operative layers therebetween;
    the plurality of operative layers comprising no more than two operative layers, the no more than two operative layers comprising:
        a first operative layer in contact with the first support layer and in vertical alignment with the sample receiving port, the first operative layer comprising a material for receiving a fluid sample containing the analyte of interest; and
        a second operative layer having a first side at least partially in contact with the first operative layer, and an opposite side in contact with the second support layer and in vertical alignment with the reaction viewing port, the second operative layer comprising a reaction membrane for receiving the analyte of interest through the first operative layer, the second operative layer containing a reagent for reacting with the analyte of interest to produce a measurable change in color for display in the reaction viewing port.

2. The test strip of claim 1, wherein the first operative layer is secured to the first support layer.

3. The test strip of claim 1, wherein the second operative layer is secured to the second support layer.

4. The test strip of claim 1, wherein the first operative layer comprises a material for spreading the fluid sample so as to evenly distribute the analyte of interest to the reaction membrane.

5. The test strip of claim 1, wherein the first operative layer comprises a cloth or a fabric.

6. The test strip of claim 1, wherein the first operative layer is treated with a chemical solution for separating at least one undesirable element from the fluid sample.

7. A test strip of claim 6, wherein the chemical solution comprises a red blood cell binding agent for capturing red blood cells from the fluid sample.

8. The test strip of claim 7, wherein the red blood cell binding agent comprises lectins.

9. The test strip of claim 1, wherein the reaction membrane comprises an isotropic membrane such that the membrane has a substantially uniform porosity.

10. The test strip of claim 9, wherein the membrane comprises polysulfone.

11. The test strip of claim 1, wherein the reagent comprises a reactant for facilitating an end-point test in a corresponding reflectance meter.

12. The test strip of claim 11, wherein the reagent includes an enzyme solution.

13. The test strip of claim 1, wherein the reagent is capable of detecting glucose analytes in the fluid sample.

14. The test strip of claim 13, wherein the reagent includes an indicator chemical capable of visually indicating the amount of glucose analytes in the fluid sample.

15. The test strip of claim 1, wherein the reagent is capable of detecting at least one of: cholesterol analytes in the fluid sample; osteoporosis analytes in the fluid sample; ketones analytes in the fluid sample; theophylline analytes in the fluid sample; H1AC analytes in the fluid sample; or fructosamine analytes in the fluid sample.

16. The test strip of claim 1, wherein the measurable change in the reagent corresponds to the amount of analyte of interest present.

17. The test strip of claim 1, further comprising indicia for indicating a proper orientation for insertion of the test strip in a corresponding meter.

18. The test strip of claim 17, wherein the indicia comprises an arrow on the first support layer to indicate proper direction of insertion.

19. The test strip of claim 18, wherein the indicia comprises a light absorbing medium on an exposed surface of the first support layer.

20. The test strip of claim 19, wherein the light absorbing medium comprises a black region proximate an end of the first support layer.

21. The test strip of claim 1, wherein the dimensions of the test strip are adapted to accommodate a sample volume of about 3 µl or less.

22. A diagnostic test strip for providing an indication of at least one of the presence, the absence or the amount of glucose analytes in a blood sample, the test strip comprising:
   a first support layer comprising a sample receiving port for receiving the blood sample;
   a second support layer comprising a reaction viewing port for displaying the indication;
   a plurality of operative layers between the first and second support layers, the first and second support layers being secured together so as to secure the plurality of operative layers therebetween;
   the plurality of operative layers comprising no more than two operative layers, the no more than two operative layers comprising:
      a first operative layer secured to the first support layer and in vertical alignment with the sample receiving port, the first operative layer comprising a material for receiving a blood sample and for spreading the sample so as to distribute glucose analytes therein to a second operative layer; and
      the second operative layer having a first side at least partially in contact with the first operative layer, and an opposite side secured to the second support layer and in vertical alignment with the reaction viewing port, the second operative layer comprising a reaction membrane for receiving glucose analytes from the blood sample through the first operative layer, the second operative layer containing a reagent for reacting with the glucose analytes to produce a measurable change in color for display in the reaction viewing port.

23. The test strip of claim 22 wherein the sample receiving port is substantially circular.

24. The test strip of claim 22 wherein the first and second support layers are substantially rectangular.

25. The test strip of claim 22, wherein the first and second support layers are secured together by glue.

26. The test strip of claim 22, wherein the reagent comprises a reactant for facilitating an end-point test in a corresponding reflectance meter.

27. The test strip of claim 26, wherein the reagent includes an enzyme solution.

28. The test strip of claim 22, wherein the reagent is capable of detecting glucose analytes in the fluid sample.

29. The test strip of claim 28, wherein the reagent includes an indicator chemical capable of visually indicating the amount of glucose analytes in the fluid sample.

30. The test strip of claim 22, further comprising indicia for indicating a proper orientation for insertion of the test strip in a corresponding meter.

31. The test strip of claim 30, wherein the indicia comprises an arrow on the first support layer to indicate proper direction of insertion.

32. The test strip of claim 31, wherein the indicia comprises a light absorbing medium on an exposed surface of the first support layer.

33. The test strip of claim 32, wherein the light absorbing medium comprises a black region proximate an end of the first support layer.

34. The test strip of claim 22, wherein the dimensions of the test strip are adapted to accommodate a sample volume of about 3 µl or less.

* * * * *